US00PP21734P2

(12) United States Plant Patent
Smith

(10) Patent No.: US PP21,734 P2
(45) Date of Patent: Feb. 22, 2011

(54) *SALVIA* PLANT NAMED 'FERPINK'
(50) Latin Name: *Salvia leucantha*
Varietal Denomination: FERPINK

(76) Inventor: Ian Smith, "Sandvliet", Valleifontein, Lichtenburg District (ZA)

( * ) Notice: Subject to any disclaimer, the term of this patent is extended or adjusted under 35 U.S.C. 154(b) by 3 days.

(21) Appl. No.: 12/383,631

(22) Filed: Mar. 26, 2009

Related U.S. Application Data

(60) Provisional application No. 61/123,113, filed on Apr. 3, 2008.

(51) Int. Cl.
*A01H 5/00* (2006.01)

(52) U.S. Cl. ..... Plt./475

(58) Field of Classification Search ..... Plt./475
See application file for complete search history.

*Primary Examiner*—Kent L Bell

(57) ABSTRACT

A new and distinct cultivar of *Salvia leucantha* named 'FERPINK' whose foliage and form are typical of the species but whose flowers are pink with white calyces.

2 Drawing Sheets

Genus: *SALVIA.*
Species: *leucantha.*
Denomination: 'FERPINK'.

BACKGROUND OF THE INVENTION

This application is co-pending with the same inventor's non-provisional application entitled *SALVIA* plant named 'FERWHITE', application Ser. No. 12/383,635.

The present invention relates to a new and distinct cultivar of *Salvia leucantha*, commonly known as Mexican bush sage, hereinafter referred to by the cultivar name, 'FERPINK'. The inventor discovered 'FERPINK' in 2003 in the inventor's garden in Sandvliet, Lichtenburg District, South Africa. 'FERPINK' was discovered as a naturally occurring single plant with novel pink flowers which the inventor found growing amongst many other self-sown plants of the typically purple-flowered species *Salvia leucantha* (species, unpatented). The parents of 'FERPINK' are unknown.

'FERPiNK' is slightly less vigorous than plants of the species, has mid-green leaves and pink flowers which are more abundant when the plant is grown in full sun.

'FERPINK' may be compared with its species and with all other varieties of *Salvia leucantha* known to the inventor as follows: Whereas the species and all other varieties of *Salvia leucantha* known to the inventor excluding the co-pending variety, *Salvia* 'FERWHITE' exhibit purple-violet calyces and white flowers, the flowers of 'FERPINK' exhibit white calyces and pink flowers. The flowers of 'FERWHITE' exhibit white calyces and white flowers.

'FERPINK' was first asexually propagated according to the inventor's directions in 2003 in a garden in Klein Optenhorst, Wellington, South Africa using tip cuttings from the originally discovered plant. The inventor has determined that 'FERPINK' is stable and reproduces true to type in successive generations of asexual reproduction.

The inventor filed an application for PBR in South Africa on Sep. 5, 2006, Ser. No. PT 4852, which has since matured into a grant of rights, ZA 20083844, dated Mar. 25, 2008. No plants were sold, or offered for sale or made available to the public until Apr. 14, 2007.

SUMMARY OF THE INVENTION

The distinguishing characteristics of 'FERPINK' are as follows: In combination these traits set 'FERPINK' apart from all other existing varieties of *SALVIA leucantha* known to the inventor. 'FERPINK' has not been tested under all possible conditions and phenotypic differences may be observed with variations in environmental, climatic, and cultural conditions.

1. 'FERPINK' is perennial in temperatures above 25 degrees Fahrenheit.
2. The foliage of 'FERPINK' is gray-green in color and the leaf surfaces are deeply furrowed.
3. The flowers of 'FERPINK' are pink in color.
4. The calyx of 'FERPINK' is white in color.
5. 'FERPINK' blooms from spring to late summer, and year-round in southern California.
6. 'FERPINK' is slightly less vigorous than other forms of the species: after one year from a cutting, 'FERPINK' achieves a height of 45 cm and a width of 20 cm. When mature, 'FERPINK' achieves a height of 90 cm (120 cm including the inflorescence) and a width of 60 cm.

BRIEF DESCRIPTION OF THE DRAWINGS

The accompanying color drawings illustrate the overall appearance of 'FERPINK' showing the colors of its foliage and flowers as true as it is reasonably possible to obtain in colored reproductions of this type.

The drawing labeled as FIG. 1 depicts a nine-months old single plant of 'FERPINK' in first flower in April.

Figure 1:
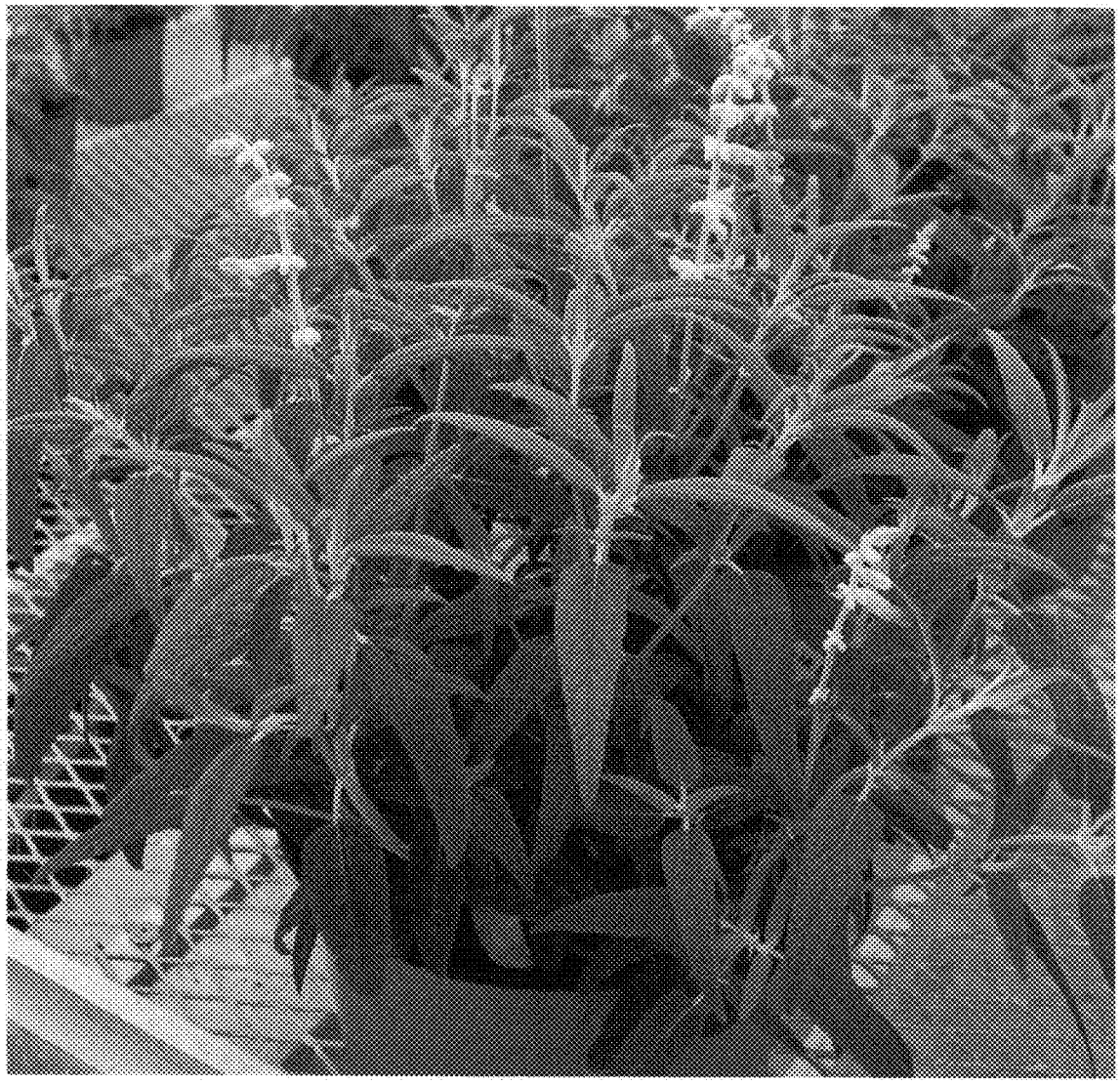
Figure 2:
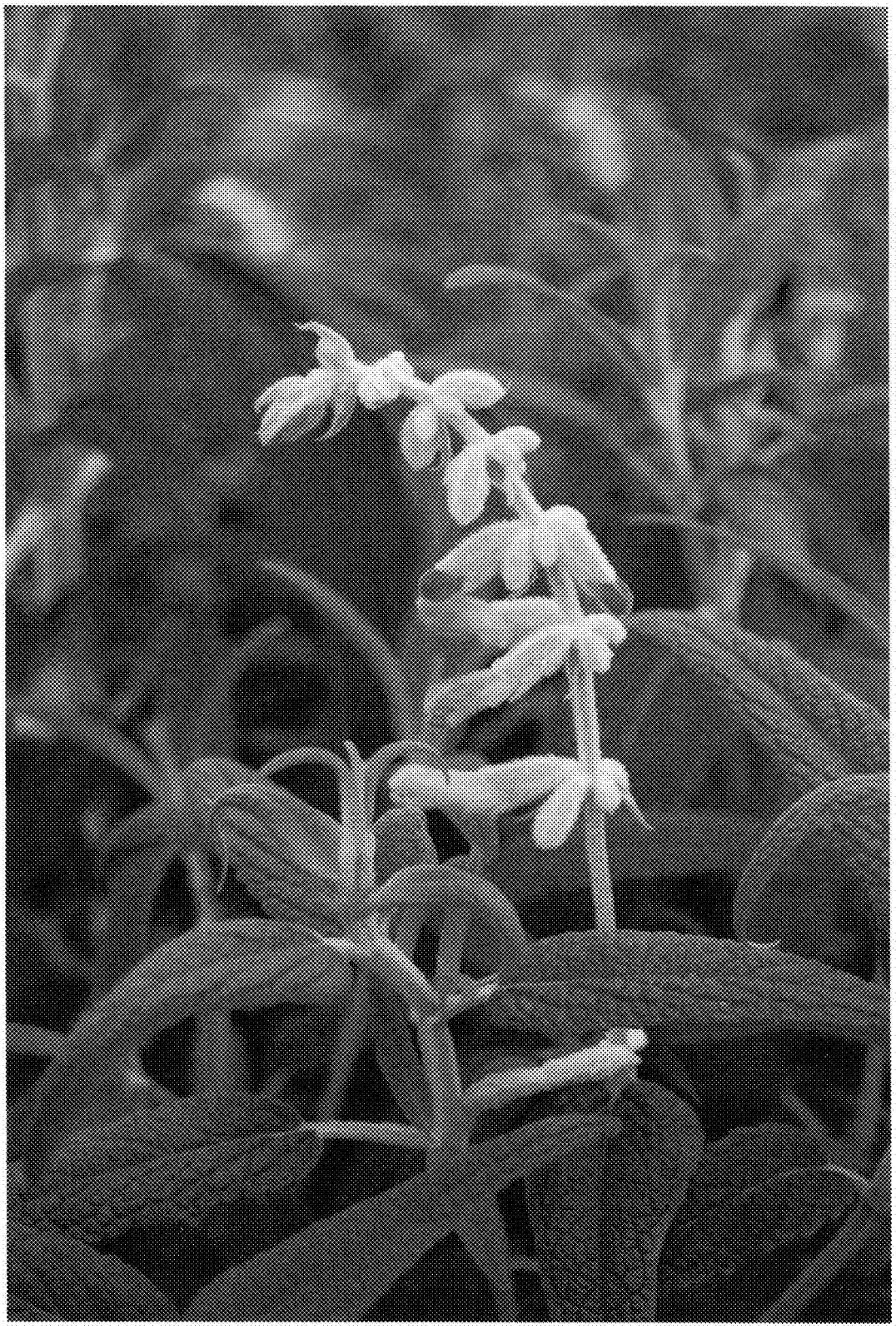

The drawing labeled as FIG. 2 depicts a close-up view of the deeply furrowed foliage, the pink flowers and the white calyx of 'FERPINK'.

Both drawings have been made from the same plant which has been grown in Watsonville, Calif.

BOTANICAL DESCRIPTION OF THE PLANT

The following is a detailed botanical description of the new *Salvia* cultivar 'FERPINK'. Observations, measurements, color determinations, and comparisons were made in Santa Barbara, Calif., from plants that were grown in one-gallon containers. Color determinations were made in accordance with The Royal Horticultural Society Colour Chart from London, England, except where general color terms of ordinary dictionary significance are used. The growing requirements of the new variety are similar to the species and there are no known growing problems.

Botanical classification: *Salvia leucantha* 'FERPINK'.

Common name: Mexican sage.

Parentage: Unknown.

Propagation method: Propagation is accomplished by the methods of division and tip cuttings.

Rooting habit: Fine and fibrous.

Time to develop roots: Approximately 20 days are required to develop roots from an initial tip cutting.

Crop time: Six months are required to achieve a finished one-gallon container from an initial tip cutting.

Pest and disease resistance or susceptibility: 'FERPINK' is not susceptible to any pests or diseases known to the inventor.

Plant habit: Moderately spreading.

Use: For planting in containers and for growing in the garden and landscape.

Type: Perennial herb.

Growth rate: Moderate to vigorous.

Dimensions of plant:

*After* 1 *year.*—Height (including the inflorescence): 45 cm, width 20 cm.

*When mature.*—Height 90 cm (120 cm including the flowers), width 60 cm.

Hardiness: USDA Zone 9.

Plant habit: Multiple stems arise from rootstock with many lateral branches on each stem.

Stems:

*Color.*—Ranges from 139A when juvenile to 146A when mature.

*Shape.*—Terete.

*Diameter.*—4 mm.

*Length.*—25 cm.

*Surface.*—Pubescent, hairs fine and white, less than 1 mm in length.

Lateral branches: As stems, except.

*Length.*—15 cm.

*Internode distance.*—3-5 cm.

Foliage:

*Leaf arrangement.*—Opposite.

*Leaf division.*—Simple.

*Leaf shape.*—Linear to ovate.

*Leaf length.*—7-9 cm. in length.

*Leaf width.*—1 cm. in width.

*Leaf tip.*—Acute.

*Leaf base.*—Rounded.

*Leaf venation pattern.*—Reticulate with prominent midvein protruding on lower surface and depressed on upper surface.

*Vein color* (*adaxial surface*).—138A.

*Vein color* (*abaxial surface*).—138B.

*Margin type.*—Crenulate.

*Leaf surface* (*adaxial surface*).—Deeply furrowed, lightly pubescent.

*Leaf surface* (*abaxial surface*).—Furrowed, moderately pubescent, hairs white.

*Leaf attachment.*—Petiolate.

*Petiole dimensions.*—3-4 mm. in length and 1.5 mm. in width.

*Petiole surface.*—Pubescent.

*Petiole color.*—Pubescent, hairs appear white.

*Leaf color* (*adaxial*).—141A.

*Leaf color* (*abaxial*).—138B.

Inflorescence:

Form: Raceme.

Dimensions.—25 cm-30 cm in length; 4 cm-8 cm in diameter.

Flower arrangement: Flowers are arranged in whorls, as is typical of the species and its known cultivars.

Quantity of flowers: A range of 7-9 flowers per whorl and a range of 8-20 whorls per raceme.

Distance between whorls: 1.0 cm. to 2.5 cm.

Flowering season: Year round in Southern California and spring to summer elsewhere.

Lastingness of the flowers (on the plant): From 8 days in spring to 3 days in summer.

Aspect: Facing outward.

Flower:

*Attachment.*—Sessile.

*Bud shape.*—Pandurate.

*Bud color* (*no flower emerging*).—192B, appears lighter due to white pubescence.

*Bud surface.*—Highly pubescent, many fine white hairs, appears woolly or velvety.

*Bud dimensions.*—3-4 mm. in diameter and 7 mm. in length.

*Shape of corolla tube.*—Tubular.

*Surface of corolla tube:.*—Pubescent.

*Corolla tube color.*—Ranges from 155C at base and extending 4 mm, then N57D.

*Flower dimensions* (*calyx, corolla tube, and extended lower lip with lobes*).—4 cm. in length and 1 cm. in diameter.

*Number of corolla lobes.*—Two primary lobes and two reduced lateral lobes.

*Lobe dimensions.*—Primary lobe: length 4 mm, width 2 mm. Reduced lateral lobe: length 2 mm, width 1 mm.

*Lobe apex* (*all lobes*).—Rounded.

*Lobe margin* (*all lobes*).—Entire.

*Color of lobes* (*both surfaces*).—N57D.

*Number of petals.*—Two in number.

*Petal dimensions.*—13 mm-15 mm in length, 4 mm-7mm in width.

*Petal apex.*—Rounded.

*Petal margin.*—Entire.

*Color of petals* (*both surfaces*).—Ranges between N57B (newly emerging) to N57D.

*Petals fused or unfused.*—Petals are basally fused.

*Shape of petals.*—Spatulate.

*Peduncle dimensions.*—2.5 mm. in width by 25 cm. in length.

*Peduncle shape.*—Terete.

*Peduncle surface.*—Pubescent, hairs white and concentrated towards apex.

*Peduncle color.*—138C, appearing more white towards apex due to more concentrated pubescence.

*Calyx shape.*—Tubular.

*Calyx dimensions.*—1 cm. in length and 0.5 cm. in diameter.

*Calyx color* (*both surfaces*).—192B.

*Calyx surface* (*outer surface*).—Pubescent, hairs fine and white.

*Calyx surface* (*inner surface*).—Smooth (pubescence absent).

*Number of sepals.*—2, basally fused, color (both surfaces) 192B.

*Sepal dimensions.*—5 mm in length, 5 mm in width.

*Sepal shape.*—Deltoid.

*Sepal apex.*—Acuminate.

*Sepal margin.*—Smooth.

Reproductive organs:

*Pistil.*—One, 10 mm in length, less than 1 mm. in diameter, white.

*Stigma.*—Two unequal lobes, white.

*Style.*—Included, clavate, pubescent, appears bearded white.

*Stamens.*—Two in number, included and fused at the base.

*Anther.*—Ovoid, 2.5 mm. in length and 1 mm. in width, cream.

*Pollen.*—Low amount, mustard color.

*Ovary.*—Shape terete, length 1.5 mm, width 1 mm, color 150D.

Seed: Seed has not been observed.

The invention claimed is:

1. A new and distinct variety of *Salvia* plant named 'FER-PINK', as illustrated and described.

* * * * *